(12) United States Patent
Hively

(10) Patent No.: US 8,416,086 B2
(45) Date of Patent: Apr. 9, 2013

(54) METHODS FOR IMPROVED FOREWARNING OF CONDITION CHANGES IN MONITORING PHYSICAL PROCESSES

(75) Inventor: Lee M. Hively, Philadelphia, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 434 days.

(21) Appl. No.: 12/872,471

(22) Filed: Aug. 31, 2010

(65) Prior Publication Data

US 2012/0050045 A1 Mar. 1, 2012

(51) Int. Cl.
G08B 23/00 (2006.01)

(52) U.S. Cl.
USPC ........ 340/573.1; 702/190; 702/191; 600/544; 600/545

(58) Field of Classification Search ............... 340/573.1; 702/190, 191; 600/544, 545
See application file for complete search history.

(56) References Cited

U.S. PATENT DOCUMENTS

| | | | |
|---|---|---|---|
| 4,792,761 A | 12/1988 | King et al. | |
| 5,349,962 A | 9/1994 | Lockard et al. | |
| 5,743,680 A | 4/1998 | Von Haas et al. | |
| 5,815,413 A * | 9/1998 | Hively et al. | 702/191 |
| 5,857,978 A | 1/1999 | Hively et al. | |
| 6,411,566 B1 | 6/2002 | Katz et al. | |
| 6,484,132 B1 * | 11/2002 | Hively et al. | 702/190 |
| 6,507,754 B2 | 1/2003 | Le Van Quyen et al. | |
| 7,139,677 B2 * | 11/2006 | Hively et al. | |
| 7,209,861 B2 * | 4/2007 | Hively et al. | |
| 7,231,254 B2 | 6/2007 | DiLorenzo | |
| 7,336,804 B2 | 2/2008 | Steffin | |
| 7,713,213 B2 | 5/2010 | Siejko et al. | |
| 2004/0087835 A1 * | 5/2004 | Hively | |
| 2009/0249128 A1 | 10/2009 | Heckman et al. | |

FOREIGN PATENT DOCUMENTS

| | | |
|---|---|---|
| CN | 101221066 A | 7/2008 |
| RU | 2008 135 566 A | 3/2010 |

OTHER PUBLICATIONS

Sheila M. Bird, et al., "Performance indicators: good, bad, and ugly", Journal of the Royal Statistical Society: Series A (Statistics in Society), Dec. 15, 2004, vol. 168, Issue 1, pp. 1-27.

Lloyd D. Johnston, et al., The Aims and Objectives of the Monitoring the Future Study and Progress Toward Fullfilling Them, 1996, Second Edition, paper 34.

* cited by examiner

*Primary Examiner* — Daniel Wu
*Assistant Examiner* — Israel Daramola
(74) *Attorney, Agent, or Firm* — Boyle Fredrickson, S.C.

(57) ABSTRACT

This invention teaches further improvements in methods for forewarning of critical events via phase-space dissimilarity analysis of data from biomedical equipment, mechanical devices, and other physical processes. One improvement involves objective determination of a forewarning threshold ($U_{FW}$), together with a failure-onset threshold ($U_{FAIL}$) corresponding to a normalized value of a composite measure (C) of dissimilarity; and providing a visual or audible indication to a human observer of failure forewarning and/or failure onset. Another improvement relates to symbolization of the data according the binary numbers representing the slope between adjacent data points. Another improvement relates to adding measures of dissimilarity based on state-to-state dynamical changes of the system. And still another improvement relates to using a Shannon entropy as the measure of condition change in lieu of a connected or unconnected phase space.

14 Claims, 5 Drawing Sheets

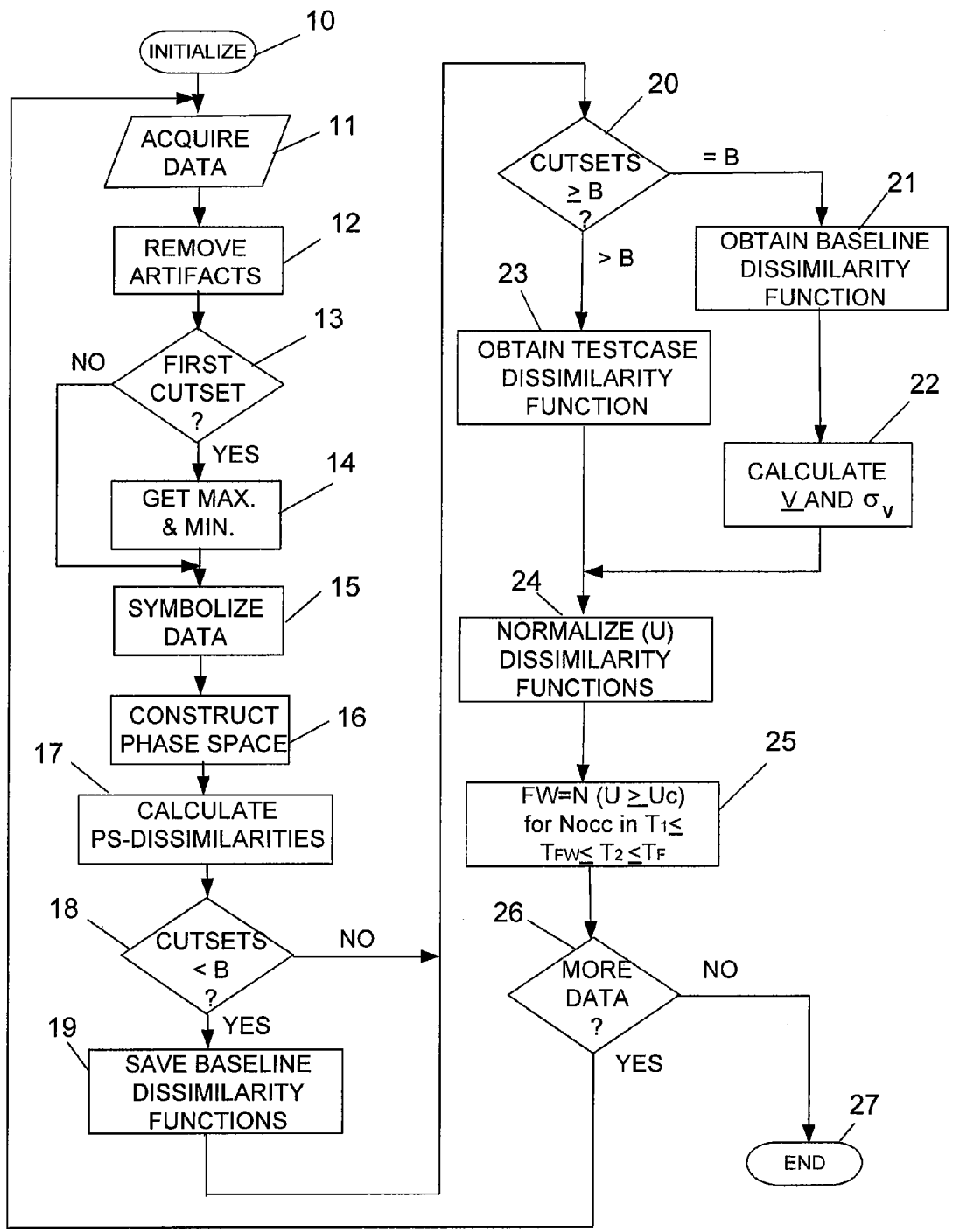
PRIOR ART  Fig. 1A

US 8,416,086 B2

METHODS FOR IMPROVED FOREWARNING OF CONDITION CHANGES IN MONITORING PHYSICAL PROCESSES

STATEMENT REGARDING FEDERALLY SPONSORED RESEARCH

This invention was made with assistance under Contract No. DE-AC05-00OR22725 with the U.S. Department of Energy. The Government has certain rights in this invention.

BACKGROUND OF THE INVENTION

The field of the invention is methods of computer analysis for forewarning of condition changes, including critical events, such as epileptic seizures in human medical patients, and including failures in machines and other physical processes.

Hively et al., U.S. Pat. Nos. 5,743,860 and 5,857,978 disclose methods for detecting and predicting epileptic seizures by acquiring brain wave data from a patient, and analyzing the data with traditional nonlinear methods.

Hively et al., U.S. Pat. No. 5,815,413, disclosed the use of phase space dissimilarity measures (PSDM) to forewarn of impending epileptic events from scalp EEG in ambulatory settings. Hively et al., U.S. Pat. No. 5,815,413, also discloses the applicability of nonlinear techniques to monitor machine conditions such as the condition of a drill bit or the performance of an electrical motor driving a pump.

Hively, U.S. Pat. No. 7,139,677, introduced a composite measure of dissimilarity (C). This composite measure of condition change (C) was calculated from the sum of the four normalized measures of dissimilarity, including $U(\chi_C^2)$ and $U(L_C)$ from the connected phase space and including $U(\chi_N^2)$ and $U(L_N)$ from the non-connected phase space. This was developed further across multiple data channels in Hively, U.S. Pat. No. 7,209,861, where the composite measure of dissimilarity, (C), was used to provide an end-of-life forewarning factor (G).

SUMMARY OF THE INVENTION

The present invention uses prior advances in the application of phase space dissimilarity measures to provide forewarning indications. In this method, forewarning of a biomedical event or machine failure is indicated at time ($T_{FW}$) after $N_{FW}$ successive occurrences of the composite dissimilarity measure ($C_i$) above a threshold ($U_{FW}$). Following receipt of the forewarning, detection of the event onset at time ($T_{FAIL}$) is indicated after $N_{FAIL}$ successive occurrences of the composite dissimilarity measure above a threshold ($U_{FAIL}$); and a visual or audible signal is provided to a human observer.

In a further aspect of the invention, the normalized measures of dissimilarity for distribution functions are based on data that are processed to discrete states on the basis of a slope between each pair of data points, which is either positive or negative depending on a change in the data between two points in time.

In a further aspect of the invention, the composite measure of dissimilarity is computed from a plurality of normalized measures of dissimilarity, wherein the measures of dissimilarity include $\chi_t^2$, $\chi_e^2$, $L_t$ and $L_e$, and where $\chi_t^2$ and $L_t$ incorporate a probability of changes of state in the sets of data from one time to another; and $\chi_e^2$ and $L_e$ represent a comparison of an equilibrium state to the present state in the sets of data.

In a further aspect of the invention, prior to the computation of the measures of dissimilarity, and in lieu of computing either a connected or unconnected phase space, a Shannon entropy is computed according to the following expression $$\Delta E = -\sum_J \{[A_J(t+\Delta t) - A_J(t)]/n\} H_J(t)$$

where E is the entropy, $A_J(t)$ is a state of the data at time t, and $H_J(t)$ is the harmonic mean.

Forewarning indications are used to forewarn of critical events, such as various biomedical events. Typical biomedical events and sources of data include, but are not limited to, epileptic seizures from EEG, cardiac fibrillation from EKG, and breathing difficulty from lung sounds.

The methods of the present invention are also applicable to machines including, but are not limited to, motors, pumps, turbines, and metal cutting. Typical time-serial machine data includes, but are not limited to, electrical current, voltage, and power; position, velocity, and acceleration; and temperature and pressure. Other physical processes capable of being monitored by sensors can also be observed to forewarn of malfunctions or failures.

Other objects and advantages of the invention, besides those discussed above, will be apparent to those of ordinary skill in the art from the description of the preferred embodiments, which follows. In the description reference is made to the accompanying drawings, which form a part hereof, and which illustrate examples of the invention. Such examples, however, are not exhaustive of the various embodiments of the invention, and therefore reference is made to the claims, which follow the description for determining the scope of the invention.

BRIEF DESCRIPTION OF THE DRAWINGS

FIG. 1A is a flow chart of a generalized prior art method;

DETAILED DESCRIPTION OF THE PREFERRED EMBODIMENTS

Figure 4:
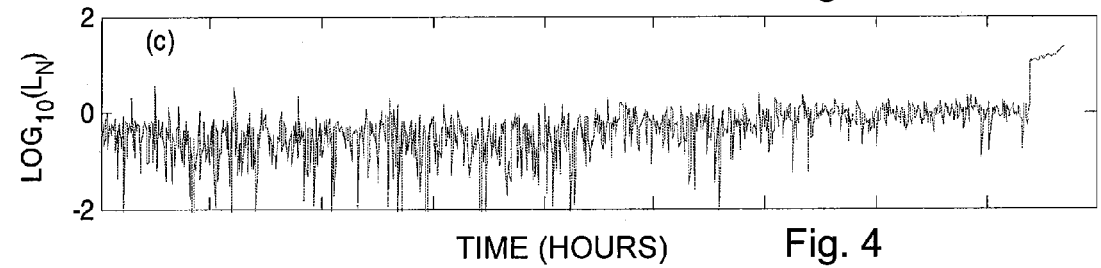
FIG. 4 is a graph of a normalized $L_N$ measure of dissimilarity for the non-connected phase-space, $U(L_N)$ versus time for the same accelerometer channel as FIG. 2.
Figure 5:
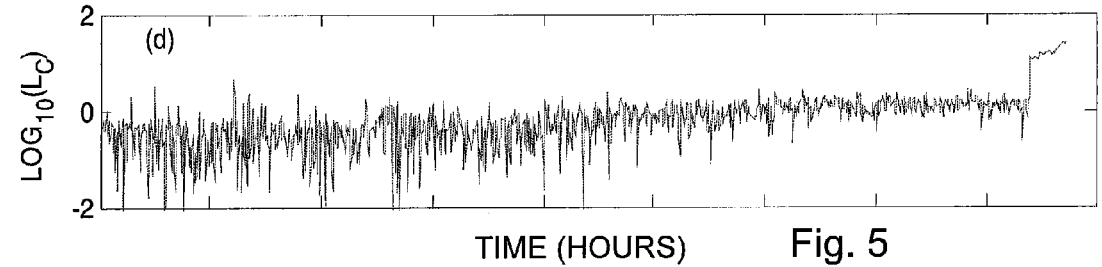
FIG. 5 is a graph of a normalized $L_C$ measure of dissimilarity for the non-connected phase-space, $U(L_C)$ versus time for the same accelerometer channel as FIG. 2
Figure 6:
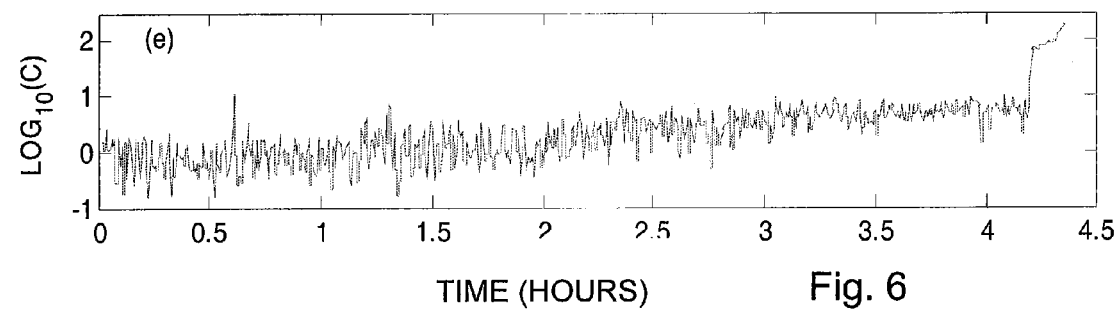
FIG. 6 is a graph of composite measure of dissimilarity, C, derived from the sum of the four measures of dissimilarity $L_N$, $L_C$, $\chi_N^2$, and $\chi_C^2$.

FIG. 1A illustrates a generalized form of a known process for providing detection of a condition change, such as a critical biomedical event or a machine critical event. This process is disclosed in prior patents of the inventor herein, which are referred to in the Background of the Invention, including U.S. Pat. No. 6,484,132, FIG. 4 and accompanying description, which is incorporated herein by reference. As shown generally in FIG. 1A, the process, which is carried out in computing apparatus in FIG. 10 to be described below, through execution of a program of computer instructions, represented by the blocks in FIG. 1A, including an initialization of parameters step represented by start block 10. Next, as represented by I/O block 11, data are acquired or input, in the form of a process-indicative scalar signal, e, which is sampled at equal time intervals, $\tau$, starting at an initial time, $t_0$, yielding a sequence of N points, called a "cutset," $e_i = e(t_0 + i\tau)$. This is a subset of the dataset being analyzed.

Next, as represented by process block 12, artifacts are removed from the data with a zero-phase quadratic filter that performs better than conventional filters. This filter uses a moving window of 2w+1 points of data, with the same number of data points, w, on either side of a central point. A parabola is fitted in the least-squares sense to these data points, and the central point is selected to estimate the low-frequency artifact, $f_i$. The residual (artifact-filtered) signal, $g_i = e_i - f_i$, has essentially no low-frequency artifact activity. All subsequent analysis uses this artifact-filtered data, $g_i$. This is known in the art from U.S. Pat. No. 5,626,145.

Each artifact-filtered point is converted into a discrete symbol, $s_i$, as one of S different integers in the range, $0 \leq s_i \leq S-1$. A test is then made for whether this is the first cutset of data as represented by decision block 13. If so, as represented by the "YES" result, the minimum, $g_{min}$, and maximum, $g_{max}$, in the data are calculated of the first baseline cutset as represented by process block and 14 in FIG. 1. Contiguous, non-overlapping partitions are selected to obtain uniform symbols: $s_i = \text{INT}[S\ (g_i - g_{min})/(g_{max} - g_{min})]$ for $g_i < g_{max}$, and $s_i = S-1$ for $g_i = g_{max}$ to maintain exactly S discrete symbols as represented by process block 15 in FIG. 1. The function, INT, converts a decimal number to the next lowest integer [e.g., INT (3.14)=3].

Assuming, the first cutset has been processed, the next step is to symbolize the data as represented by process block 15. Equiprobable symbols are formed by ordering all N of the base case artifact-filtered, time-serial data points from the smallest to largest value. The first N/S of these ordered values correspond to the first symbol, 0. Ordered data values (N/S)+1 through 2N/S correspond to the second symbol, 1, and so on. Equiprobable symbols have non-uniform partitions in the signal amplitude with the same occurrence frequency of $g_i$ values by construction, and thus have no information about the dynamical structure. In contrast, symbols with uniform partitions (uniform symbols), $s_i = S(g_i - g_{min})/(g_{max} - g_{min})$, have inherent dynamical structure before beginning the (PS) reconstruction, where $g_{max}$ and $g_{min}$ are the maximum and minimum values of the $g_i$-data, respectively. Thus, one advantage of equiprobable symbols is that dynamical structure arises only from the PS reconstruction, as described below. Moreover, large negative and large positive values of $g_i$ have little effect on equiprobable symbolization, but dramatically change the partitions for uniform symbols.

Next, as represented by process block 16, the time-serial $s_i$-data are converted into a geometric object via phase-space (PS) reconstruction that uses time-delay vectors with the form, $$y(i) = [s_i, s_{i+\lambda}, \ldots, s_{i+(d-1)\lambda}], \quad (1)$$

which partitions the PS into $S^d$ hypercubes or bins. Each bin (or state) can be identified by a unique integer, J, via base-S arithmetic, namely, $J = \Sigma_m s_{i+m\lambda} S^m$, where the summation, $\Sigma_m$, is over the range $0 \leq m \leq d-1$. Additional data channels may add more information about the inter-connected brain dynamics, implying that a multi-channel PS-vector could contain more information than a single channel. The multi-channel PS vector takes the form:

$$y(i) = [s_i(1), s_{i+\lambda}(1), \ldots, s_{i+(d-1)\lambda}(1), \ldots, s_i(Ch.), s_{i+\lambda}(Ch.), \ldots, s_{i+(d-1)\lambda}(Ch.)] \quad (2)$$

Here, the symbol, s(k) denotes values from the k-th channel, i.e., $1 \leq k \leq Ch.$, where Ch. is the total number of data channels. Now, the symbolization divides the multi-channel PS in $S^{Cd}$ bins, where the bin identifier is $J = \Sigma_k \Sigma_m s_{i+m\lambda}(k) S^{m+d(k-1)}$. The choice of lag, $\lambda$, and embedding dimension, d, determines how well the PS reconstruction unfolds the dynamics. An excessively large embedding dimension could result in over-fitting of real data with finite length and noise.

Conversion of the time-serial data into discrete PS states allows the construction of a statistical distribution function (DF), as represented by process block 17, by counting the number of PS points that occur in each bin.

The population of the ith bin of the DF, is denoted as Qi, for the base case, and Ri for a test case, respectively. An (un) changing DF indicates (un)altered dynamics. We save the DFs from first B cutsets as baseline DFs as represented by blocks 19 in FIG. 1, to represent the nominal dynamics. As represented by decision block 20, when the number of cutsets equals the statistical sample number, B, the baseline dissimilarity calculations are completed as represented by process block 21.

Then, the baseline DFs are exhaustively compared to one another in pair-wise fashion via the dissimilarity measures (DM) of Eqs. (3)-(6) below as represented by block 22 in FIG. 1, to obtain the mean baseline dissimilarity, V, and a corresponding standard deviation, $\sigma$, for each DM from the set, $V = \{L_N, L_C, \chi_N^2, \chi_C^2\}$. When the next cutset is detected in decision block 20, it becomes the test case. In a similar fashion, we obtain the dissimilarity functions as represented by block 23, between DFs for the baseline, Qi, and test case, Ri, respectively. One set of dissimilarity measures (DM) for the non-connected phase space is:

$$\chi_N^2 = \sum_J (Q_J - R_J)^2 / (Q_J + R_J), \quad (3)$$

$$L_N = \sum_J |Q_J - R_J|. \quad (4)$$

The summations in Eqs. (3)-(4) run over all of the populated PS bins. The $\chi^2$ statistic is one of the most powerful, robust, and widely used tests for dissimilarity between two distribution functions (DFs). In this work, $\chi^2$ is not an unbiased statistic for accepting or rejecting a null statistical hypothesis but rather is a relative measure of dissimilarity between the two distribution functions (DFs). The $L_1$ distance is the natural metric for the distribution functions (DFs) by its direct relation to the total invariant measure on the attractor. These measures account for changes in the geometry and visitation frequency of the attractor. Consistent calculation requires the same number of points in both the base and test case distribution functions (DFs), identically sampled; otherwise the distribution functions must be rescaled.

The accuracy and sensitivity of the PS reconstruction can be enhanced by connecting successive PS points as prescribed by the underlying dynamics, $y(i) \rightarrow y(i+\mu)$, for $\mu \geq 1$. Thus, we obtain a discrete representation of the process flow $Y(i)=[y(i), y(i+\mu)]$ that is formed by adjoining two successive vectors from the d-dimensional reconstructed PS. $Y(i)$ is a 2d-dimensional, connected-phase-space (CPS) vector. As before, A and B denote the CPS DFs for the base case and test case, respectively. We then define the measures of dissimilarity between these two CPS DFs via the $L_1$-distance and $\chi^2$ statistic, as before:

$$\chi_C^2 = \sum_{JK} (Q_{JK} - R_{JK})^2 / (Q_{JK} + R_{JK}), \quad (5)$$

$$L_C = \sum_{JK} |Q_{JK} - R_{JK}|. \quad (6)$$

The subscript c denotes connected phase space measures in Eqs. (5)-(6), while the subscript, n, in Eqs. (3)-(4) denotes non-connected phase space measures. The subscripts, J and K, are identifiers for the two successive PS states, $y(i)$ and $y(i+\mu)$, respectively. Connected phase space measures have higher discriminating power than their non-connected counterparts. We call the quantities in Eqs. (3)-(6), phase space dissimilarity measures (PSDM). Their definitions allow PSDM to flag transitions between regular and chaotic regimes, as well as to discriminate between different chaotic regimes. While straightforward methods exist for discriminating between regular and chaotic motion, or for detecting the transition between these regimes, discriminating between close chaotic regimes via traditional nonlinear measures (e.g., Lyapunov exponents, Kolmogorov entropy, and correlation dimension) is almost impossible. The reason for the superior performance of PSDM is rather simple: tradition nonlinear measures use a difference of averages, while PSDM use sums of the absolute value of differences.

The disparate range and variability of these measures are difficult to interpret, so we need a consistent means of comparison. Thus, we normalize the dissimilarity measures by comparing each of the B baseline cutsets to each (ith) test case cutset, and then computing the corresponding average dissimilarity value, $V_i$, of the ith cutset as represented by process block 24. The normalized form is: $U(V)=|V_i-\bar{V}|/\sigma$, which is the number of standard deviations that the test case deviates from the baseline mean.

The base case corresponds to the nominal-state dynamics. V denotes a phase-space dissimilarity measure from the set, $V=\{L_N, L_C, \chi_N^2, \text{ and } \chi_C^2\}$. We obtain the mean value, $\bar{V}$, of the dissimilarity measure by comparison among the $B(B-1)/2$ unique combinations of the B base case cutsets, with a corresponding sample standard deviation, $\sigma$. We subsequently compare each contiguous, non-overlapping test case cutset to each of the B base case cutsets, and obtain the corresponding average dissimilarity value, $V_i$, of the i-th analysis window for each dissimilarity measure. A statistically significant trend in the normalized dissimilarity measure indicates equipment degradation for failure forewarning.

Once the normalized measures for the test and base cases have been obtained, a threshold, $U_{TH}$, is selected for each normalized measure U to distinguish between normal (base) and possibly abnormal regimes. The choice of a reasonable threshold is critical for obtaining robust, accurate, and timely results. A forewarning signal is obtained as represented by process block 25. The forewarning is obtained at a time, $T_{FW}$, when a normalized measure of dissimilarity exceeds the threshold, $U \geq U_{TH}$, for a specified number, $N_{OCC}$, of sequential occurrences within a preset forewarning window between times, $T_1$ and $T_2$ before a time of failure, $T_{FAIL}$, which can be expressed as follows: $T_1 \leq T_{FW} \leq T_2 \leq T_F$, as shown in process block 25.

Further analysis uses the normalized DM from the beginning of the data file, proceeding forward in time until a forewarning occurs, as defined next. A true positive (TP=1 in the sum below) is a correct forewarning of a seizure event. This forewarning occurs when the composite dissimilarity exceeds a threshold, $U_{FW}$, for a number of sequential occurrences, $N_{OCC}$, within a preset forewarning window, $T_1 \leq T_{SZ} - T_{FW} \leq T_2$, before the seizure onset time, $T_{SZ}$. This analysis uses a value of $T_1 = 1$ minute, based on input from a physician collaborator that with even one minute of forewarning, useful things could be done to help the patient medically. The corresponding forewarning time is $T_{FW}$. Recent work by Litt et al. found precursors that occur up to several hours before epileptic events. Consequently, this work uses a forewarning window out to $T_2 \leq 8$ hours before the epileptic event to obtain $\leq 5.5$ hours of forewarning before the seizure event. A false positive (FP) is a seizure forewarning in a non-event dataset, or when $T_{SZ} - T_{FW} < T_1$ or $T_{SZ} - T_{FW} > T_2$. A true negative (TN=1) corresponds to no forewarning in a non-event dataset. No forewarning in an event dataset is a false negative (FN). This analysis is repeated for each additional window of time-serial data [step (L) in FIG. 1].

As represented by decision block 26, a check is then made for more data, and if more data is available, the routine returns to block 11, to calculate the occurrence of forewarning for each dataset via the above algorithm, and then combine the results for all of the datasets. The algorithmic flow for this portion of the methodology (not shown in FIG. 1A) involves loops over $N_{OCC}$ and $U_{TH}$, each of several data channels, and over datasets. Channel-consistent forewarning 16 is determined in the ith dataset for the jth channel of the kth patient by summing the number of true instances, $T_{jk}=\Sigma i\ [TP_{ijk}+TN_{ijk}]$. The sum over datasets runs from i=1 to M(k)=number of datasets for the kth patient. The occurrence of $T_{jk} \geq 2$ indicates consistency in more than one dataset for the same patient, while $T_{jk} \leq 1$ means that the jth channel provides no such consistency. The best channel consistency is $c_k=\max(T_{jk})$, for $T_{jk} \geq 2$ and k fixed; $c_k=0$, if $T_{jk}=1$; and $c_k=1$ for patients with only one dataset. The channel-consistent total-true rate then becomes $f_T=[\Sigma_k c_k]/[\Sigma_k M(k)]$. Here, k runs over all P of the patients, weighting each dataset equally.

Figure 1B:
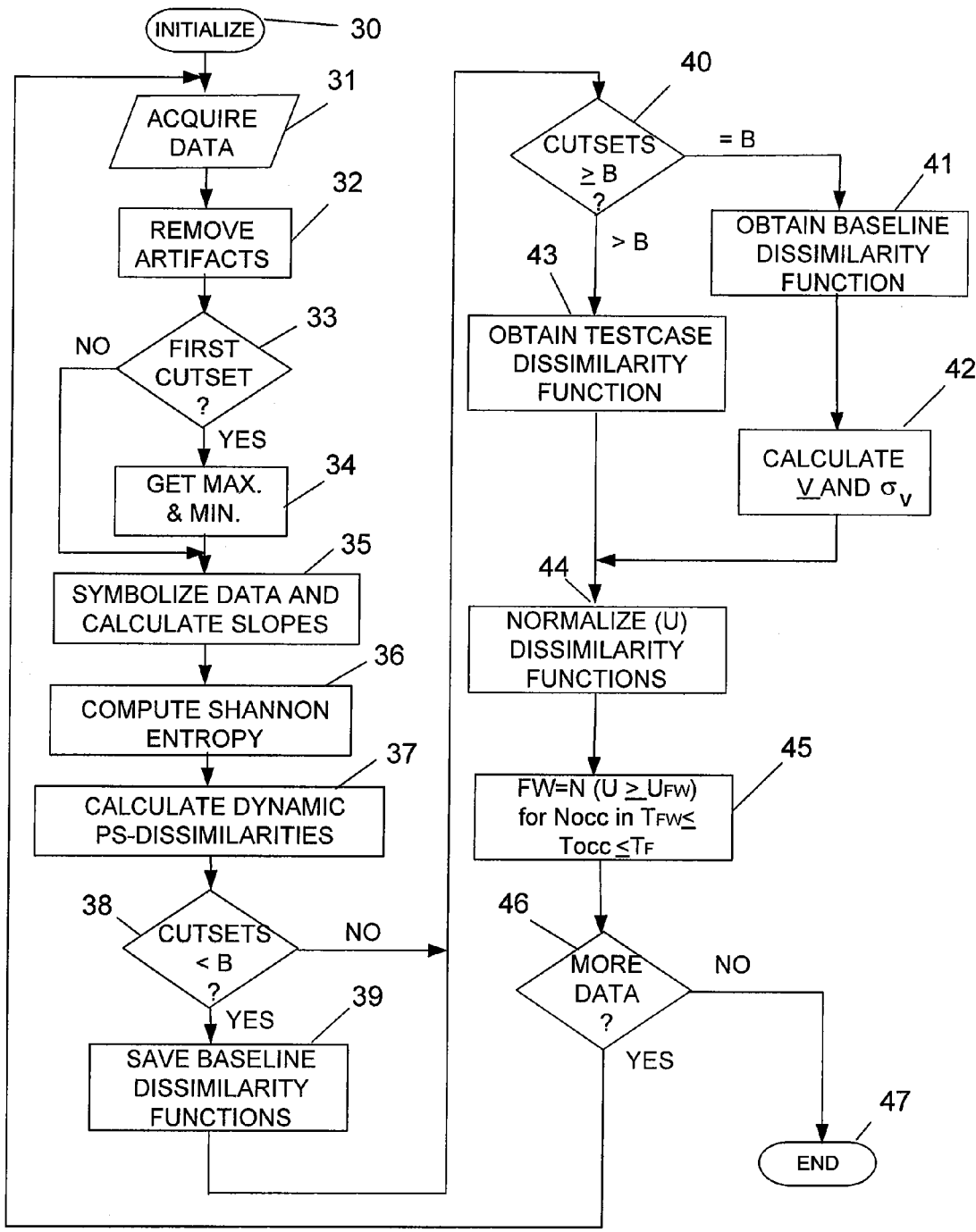
FIG. 1B is a flow chart showing improvements in the method of FIG. 1A.
Figure 2:
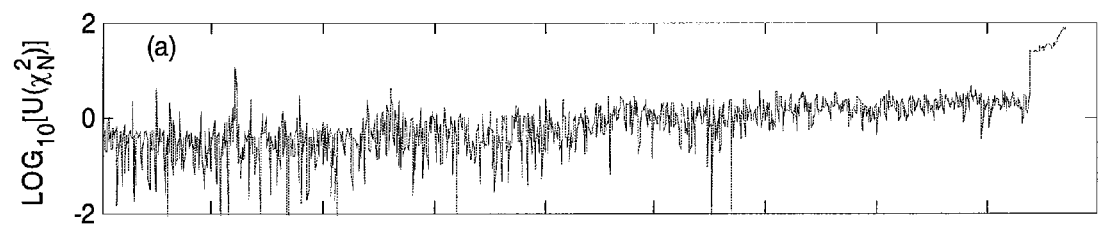
FIG. 2 is a graph of a normalized $\chi_N^2$ measure of dissimilarity for the non-connected phase-space, $U(\chi_N^2)$ versus time for an accelerometer channel, A1 with S=2, d=3, λ=18.
Figure 3:
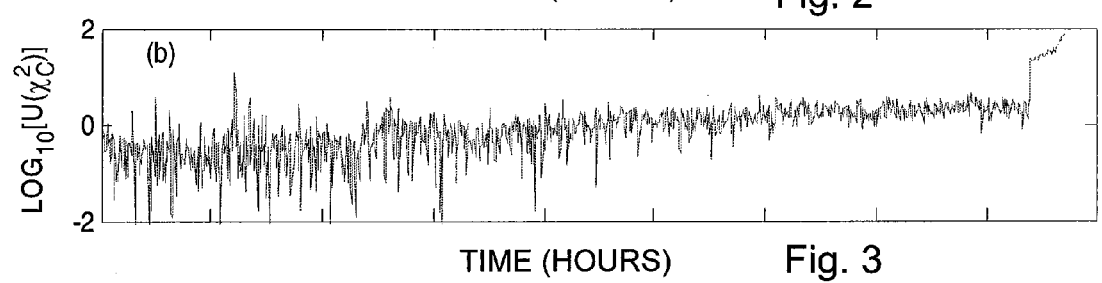
FIG. 3 is a graph of a normalized $\chi_C^2$ measure of dissimilarity for the connected phase-space, $U(\chi_C^2)$ versus time for the same accelerometer channel as FIG. 2.

FIG. 1B illustrates the method of FIG. 1A with four improvements. Blocks 30-34 correspond to the blocks 10-14 described above in relation to FIG. 1A. Blocks 38-44 also correspond to the blocks 18-24 described in relation to FIG. 1A. A first improvement to be discussed relates to the failure forewarning represented in process block 45, which adds refinement to the process block 25 in FIG. 1A.

FIGS. 2-6, display four typical phase space dissimilarity measures (PSDM) for one channel (A1) of accelerometer data from an accelerometer connected to a helicopter gearbox. The top four subplots show the individual phase space dissimilarity measures (PSDM) for $\chi_N^2$, $\chi_C^2$, $L_N$, and $L_C$. The bottom subplot shows the composite measure $(C_i)$, as a sum of the four separate phase space dissimilarity measures (PSDM):

$$C_i = U(\chi_N^2) + U(\chi_C^2) + U(L_N) + U(L_C) \quad (7)$$

It has been observed in research that $C_i$ displays the same trends as the individual PSDM and is more robust than any one of the PSDM alone. Consequently, the invention provides an improvement in the forewarning analysis focuses on the composite measure, $C_i$ which varies erratically about some nominal value. According to one aspect of the invention, failure forewarning corresponds to several successive values of $C_i$ above a threshold, the determination of which is discussed next.

Figure 7:
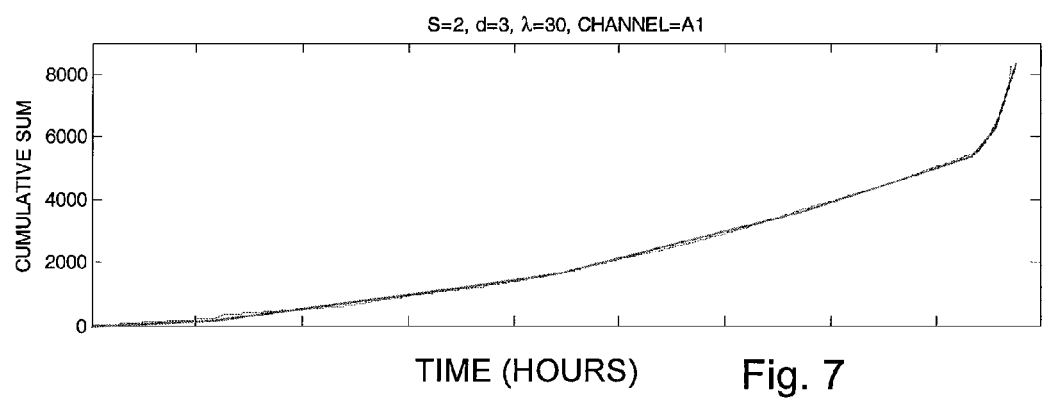
FIG. 7 is a graph of the time variation in the cumulative sum, $\Sigma_i C_i$, of the composite dissimilarity measure ($C_i$) from FIG. 6, where subscript (i) is the time index.

FIG. 7 shows $\Sigma_i C_i$, which is the cumulative sum of the composite measure from the beginning of the test to the i-th analysis window. The cumulative sum increases roughly linearly over the initial testing time. Consequently, a straight line $y_i = ai + b$ through the origin can be fitted in a least-squares calculation to the cumulative sum, $\Sigma_i C_i$.

Figure 8:
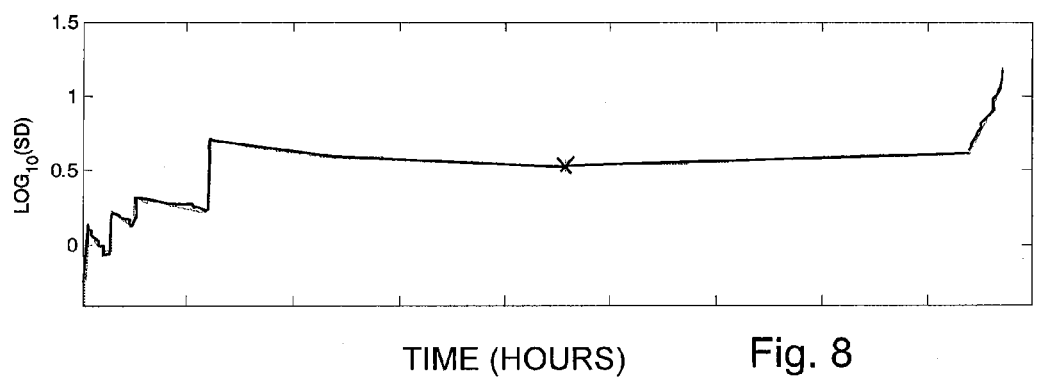
FIG. 8 is a graph of the time variation of the standard deviation (SD) of the cumulative sum from FIG. 7 and a straight-line fit through the origin, with an asterisk (*) at the local minimum, from which the forewarning threshold ($U_{TH}$) is chosen.
Figure 9:
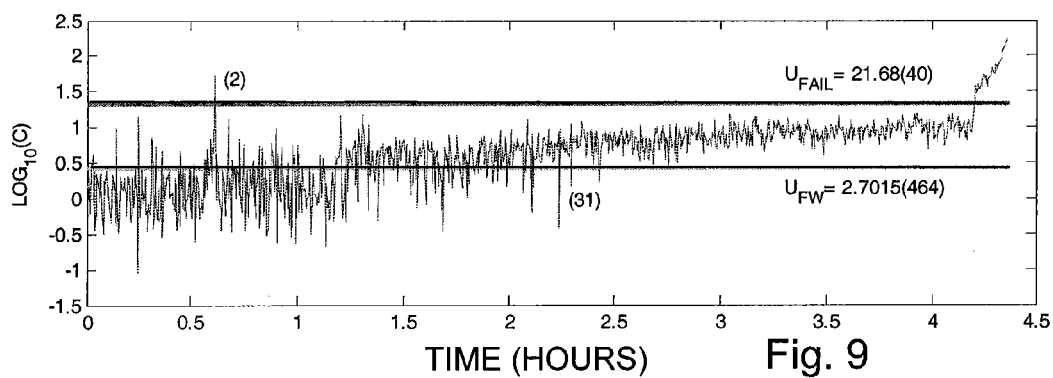
FIG. 9 is a graph of the composite PSDM versus time with a threshold for forewarning ($U_{FW}$) and another threshold for failure onset ($U_{FAIL}$)

FIG. 8 shows the standard deviation (SD) $(\sigma_1^2 = \Sigma_i(y_i - C_i)^2/(m-1))$ between the straight-line fit and the cumulative sum $\Sigma_i C_i$. The step-function jumps in the SD arise from isolated spikes in $C_i$ (in FIG. 9) during the first 1.5 hours of the test. The spikes in $C_i$ (and the resultant step-function jumps in the SD) are not statistically significant, and are ignored in the subsequent analysis. A minimum in SD occurs at 2.3 hours, as denoted by the red star (*) in the middle subplot of FIG. 8. The slope of this best-fit straight line corresponds to a threshold value, $U_{FW} = 2.7015$ (bottom horizontal line.) FIG. 9 illustrates that many $C_i$ values fall below this threshold before 2.43 hours, corresponding to normal gearbox operation. An objective determination of failure forewarning appears after that.

FIG. 9 displays failure forewarning, corresponding to $C_i > U_{FW}$ after 2.43 hours. The specific number of successive values of $C_i > U_{FW}$ after 2.43 hours is 464, which is shown inside the parentheses, next to $U_{FW} = 2.7015$ in the bottom subplot. Before 2.43 hours (specifically, between 2.3 and 2.425), the largest number of successive occurrences of $C_i > U_{FW}$ is 31, as denoted by "(31)" just below that time segment in the bottom subplot. The analysis excludes this false indication by requiring at least one more than 31 successive occurrences above the threshold. Thus, the complete forewarning criterion is $\geq 32$ successive occurrences of $C_i > U_{FW} = 2.7015$. The corresponding start of forewarning is at 2.56 hours on the basis of 32 cutsets after 2.43 hours (15 seconds per time window). The analysis searches across the phase-space parameters for the earliest forewarning time.

FIG. 9 further shows the determination of failure onset. The smallest value of $C_i$ during the failure onset period is $U_{FAIL} = 21.68$; the upper horizontal line corresponds to this failure threshold. The value of $C_i \geq U_{FAIL}$ occurs 40 times in succession. These two parameters are explicitly labeled as "$U_{FAIL} = 21.68(40)$" in the upper right of FIG. 9 (bottom). Prior to failure onset only two values occur in succession above $U_{FAIL}$, as denoted by "(2)" near the peak at 0.6 hours. Consequently, the failure-onset criterion is $\geq 3$ successive occurrences of $C_i > U_{FAIL} = 21.68$.

An example of the invention involves four channels of uni-axial acceleration data from a motor connected to a mechanical load via a gearbox. Application of excess load causes accelerated failure of the gears.

An analysis of accelerometer channels A1-A5 is summarized in Table 1 below. No forewarning or event detection was found for channel, A4.

TABLE 1

Summary of Forewarning Criteria for Each of Channels A1, A2, A3, A5 via Phase-Space Dissimilarity

| Parameter | Accelerometer Channel Designation | | | | |
|---|---|---|---|---|---|
| | A1 | A2 | A3 | A4 | A5 |
| Forewarning threshold, $U_{FW}$ | 2.7015 | 4.3122 | 2.7836 | — | 16.4579 |
| Successive occurrences above $U_{FW}$ | $\geq 32$ | $\geq 52$ | $\geq 13$ | — | $\geq 64$ |
| Threshold for failure onset, $U_{FAIL}$ | 21.68 | 27.425 | 1.2519 | — | 19.24 |
| Successive occurrences above $U_{FAIL}$ | $\geq 3$ | $\geq 10$ | $\geq 33$ | — | $\geq 24$ |
| Number of phase-space symbols, S | 2 | 2 | 11 | — | 12 |
| Dimension of phase space, d | 3 | 3 | 3 | — | 3 |
| Phase-space, time-delay lag, $\lambda$ | 30 | 10 | 12 | — | 20 |
| Start of forewarning (hours) | 2.56 | 2.58 | 4.29 | — | 4.18 |
| Longest non-forewarning time (hrs) | 2.30-2.47 | 2.15-2.36 | 1.27-1.31 | — | 2.64-2.90 |
| Start of failure indication (hours) | 4.21 | 4.24 | 4.20 | — | 4.29 |

Consequently, this novel improvement provides an objective means to obtain the thresholds for forewarning of the failure event, as well as a threshold to indicate the failure onset. The previous means used an optimization search over the various analysis parameters to maximize the total true rate, without any physical basis for determination of these thresholds.

The methods described herein can also be applied to electric motor predictive maintenance, other machinery, and physical processes. These methods can also be applied to detect condition change in patients to forewarn of epileptic seizures, cardiac problems or breathing difficulties.

A second improvement in the forewarning method of FIG. 1A concerns the symbolization step in process block 15, with the improvement being represented by process block 35 in FIG. 1B. A continuous nonlinear operation can be converted into discrete states on the basis of the slope of the signal, which is either positive or negative depending on the change in a signal between two points in time (equivalent to either 0 or 1, which are binary symbols). These discrete values can have zero slope, thus resulting in three possible symbols for each data channel (equivalent to a 0, 1, or 2, which are ternary symbols). In Table 1, channels A1 and A2 are monitored through data for three symbols. The addition of the "zero" slope (state 2) may not yield the best forewarning, but the use of symbols for rising or falling slopes or changes in the signal appears to benefit the monitoring of events subject to condition changes. The symbol partitions can become a variable, and optimized to maximize the total true rate.

Another improvement in the forewarning method of FIG. 1A concerns the calculation of the phase space dissimilarity functions $\chi_N^2$, $\chi_C^2$, $L_N$, and $L_C$ represented in process block 17, with the improvement being represented by process block 37 in FIG. 1B. This improvement involves a change in the information content in the phase-space as an alternative measure of condition change. The state-to-state transitions, $y(i) \rightarrow y(i+\mu)$, are described by the Master Equation as the time rate of change, $\partial A_J/\partial t$, in the population, $A_J$, of the J-th PS state (not necessarily the base case, in this context):

$$\frac{\partial A_J}{\partial t} = \sum_K A_K(t) r_{KJ}(t) - A_J(t) r_{JK}(t). \qquad (8)$$

Here, $A_J(t)$ is the population of the J-th PS state at time, t; $r_{JK}(t)$ is the transition rate from the J-th to the K-th state at time, t. The summation is over all possible intermediate states, K. The first term on the right hand side describes the rate of population increase due to transitions from the K-th to the J-th state; the second term on the right hand side corresponds to the population loss rate due to transitions from the J-th to the K-th states. Over a time interval, $\Delta t$, Eq. (8) becomes:

$$\Delta A_J(t) = \sum_K A_K(t) r_{KJ}(t) \Delta t - A_J(t) r_{JK}(t) \Delta t = \qquad (9)$$

$$\sum_K A_K(t) T_{KJ}(t) - A_J(t) T_{JK}(t).$$

Eq. (9) has been simplified by using $r_{JK}(t)\Delta t = T_{JK}(t)$, which denotes the transition probability from the J-th to the K-th state over the time interval, $\Delta t$. Here, $\Delta A_J$ is the change in population of the J-th state and is independent of K, thus allowing simplification to:

$$\Delta A_J(t) = \sum_K A_K(t) T_{KJ}(t) - A_J(t) \sum_K T_{JK}(t). \qquad (10)$$

The last term in Eq. (10) is the sum of all transition probabilities from the J-th to K-th states, which is unity, because (by definition) the transition matrix is normalized so that each row sum is one. We note that the transition probability, $T_{JK}(t)$, is simply the weighted adjacency matrix of the state-to-state dynamics, $T_{JK} = A_{JK}/\Sigma_K A_{JK}$, thus yielding:

$$\Delta A_J(t) = \sum_K A_K(t) T_{KJ}(t) - A_J(t). \qquad (11)$$

The population change, $\Delta A_J$ can be written as $a_J(t+\Delta t) - A_J(t)$, where $a_J(t+\Delta t)$ is a prediction for the J-th state population, and thus Eq. (11) can be simplified to:

$$a_J(t + \Delta t) = \sum_K A_K(t) T_{KJ}(t). \qquad (12)$$

The true population, $A_J(t)$, can be compared to the prediction from Eq. (12), $a_J(t)$ via $L_1$-distance and $\chi^2$ statistic, as before:

$$\chi_t^2 = \sum_J [A_J(t) - a_J(t)]^2. \qquad (13)$$

$$L_t = \sum_J |A_J(t) - a_J(t)|. \qquad (14)$$

The Perron-Frobenius Theorem (PFT) guarantees that a positive, real eigenvalue, $\lambda$, exists and has a larger magnitude than any other eigenvalue of the matrix, T, with a JK component, $T_{JK}$. The PFT further guarantees that the left eigenvector, $\rho$, corresponding to $\lambda$ has all positive components, $\rho_J$, for $\rho T = \lambda \rho$ with $\lambda = 1$, when $T_{JK} \geq 0$ and $\Sigma_K T_{JK} = 1$, as is the case here. The Ruelle-Perron-Frobenius theorem states that the equilibrium of a dynamical system corresponds to this same eigenvector, $\rho$, with a J-th state population, component, $\rho_J$, and thus Eq. (15) can be simplified to:

$$a_J(t + \Delta t) = \sum_K A_K(t) T_{KJ}(t). \qquad (15)$$

The true population, $A_J(t)$, can be compared to the prediction from Eq. (16), $a_J(t)$ via $L_1$-distance and $\chi^2$ statistic, as before:
Consequently, additional dissimilarity measures are:

$$\chi_e^2 = \sum_K [A_J(t) - \rho_J(t)]^2; \qquad (16)$$

$$L_e = \sum_K |A_J(t) - \rho_J(t)|. \qquad (17)$$

Here, the subscript, e, denotes comparison of the equilibrium state to the present state. If $L_e = \chi_e^2 = 0$, then Eqs. (16)-(17) correspond to an equilibrium state with $A_J(t) = \rho_J(t) = A_J(t+\Delta t) = a_J(t)$, implying that $L_t = \chi_t^2 = 0$ in Eqs. (13)-(14). The converse is also true. Eqs. (16)-(17) provide measures of the dynamical system's departure from equilibrium; this method uses Eqs. (13)-(17) to measure that departure from equilibrium.

Another improvement in the forewarning method of FIG. 1A concerns the construction of the phase space represented in process block 16, with the improvement being represented by process block 36 in FIG. 1B in which a Shannon entropy is computed as a measure of a system's information and dynamic change:

$$E = -\sum_J p_J \log_2 p_J. \qquad (18)$$

The relative frequency of the J-th state, $p_J$, is $p_J = A_J/n$, with $n = \Sigma_J A_J$. The time derivative of Eq. (18) then takes the form:

$$\frac{dE}{dt} = -\sum_J \left(\frac{dp_J}{dt}\right) \log_2 p_J + \sum_J \left(\frac{dp_J}{dt}\right) = -\sum_J \left(\frac{dp_J}{dt}\right) \log_2 p_J. \qquad (19)$$

The second term on the right-hand side of Eq. (19) is simplified by noting that $(p_J)(1/p_J) = 1$. Moreover, the sum and the time derivative commute, $\Sigma_J(dp_J/dt) = (d/dt)\Sigma_J p_J$. Since the sum of the relative frequencies is unity, then $(d/dt)\Sigma_J p_J = (d/dt)(1) = 0$. Eq. (19) can be converted to a change:

$$\Delta E = -\sum_J (\Delta p_J) \log_2 p_J = -\sum_J (\Delta A_J/n) \log_2 (A_J/n). \qquad (20)$$

The state change, $\Delta A_J$, might be obtained from Eq. (11). However, construction of the dynamical network via the Master equation guarantees that the number of links into a state (first term on the right hand side of Eq. (11)) is the same as the number of links away from that state (second term on the right hand side of Eq. (11)). That is, detailed balance gives $\Delta A_J=0$ for Eq. (15). Thus, the dissimilarity measures in Eqs. (13)-(14) are zero, and not useful.

A second method to determine the state change, $\Delta A_J$, is via its difference from the steady state condition from the Ruelle-Perron-Frobenius theorem, as discussed above. This approach is also inappropriate, because this steady state is indeterminate for a dynamical (non-equilibrium) system. The final option for obtaining $\Delta A_J$ is via the equation $\Delta A_J=A_J(t+\Delta t)-A_J(t)$:

$$\Delta E = -\sum_J \{[A_J(t+\Delta t) - A_J(t)]/n\} \log_2(A_J/n). \quad (21)$$

If both $A_J(t+\Delta t)$ and $A_J(t)$ are zero, then the J-th term in Eq. (20) is zero. If only one of these terms is zero (e.g., $A_J=0$), then $\log_2(A_J/n)=-\infty$. This singularity is not resolved by use of an arithmetic mean, $[\log_2 A_J(t+\Delta t) - \log_2 A_J(t)]/2$, or by a geometric mean, $\{[\log_2 A_J(t+\Delta t)][\log_2 A_J(t)]\}^{1/2}$. This singularity is resolved by the use of the harmonic mean, $H_J(t)=\langle\{1/\log_2[A_J(t+\Delta t)/n]\}-\{1/\log_2[A_J(t)/n]\}\rangle^{-1}$. Consequently, the improved version of the entropy change is:

$$\Delta E = -\sum_J \{[A_J(t+\Delta t) - A_J(t)]/n\} H_J(t). \quad (22)$$

Eq. (22) measures the information change between two successive time intervals, as a potential means to extract condition change from dynamical data.

It should be noted in FIG. 1B that the method may be identical to the method in FIG. 1A with only one of blocks 35, 36, 37 or 45 being substituted to blocks 15, 16, 17 and 25 in FIG. 1A, or any combination thereof.

Figure 10:
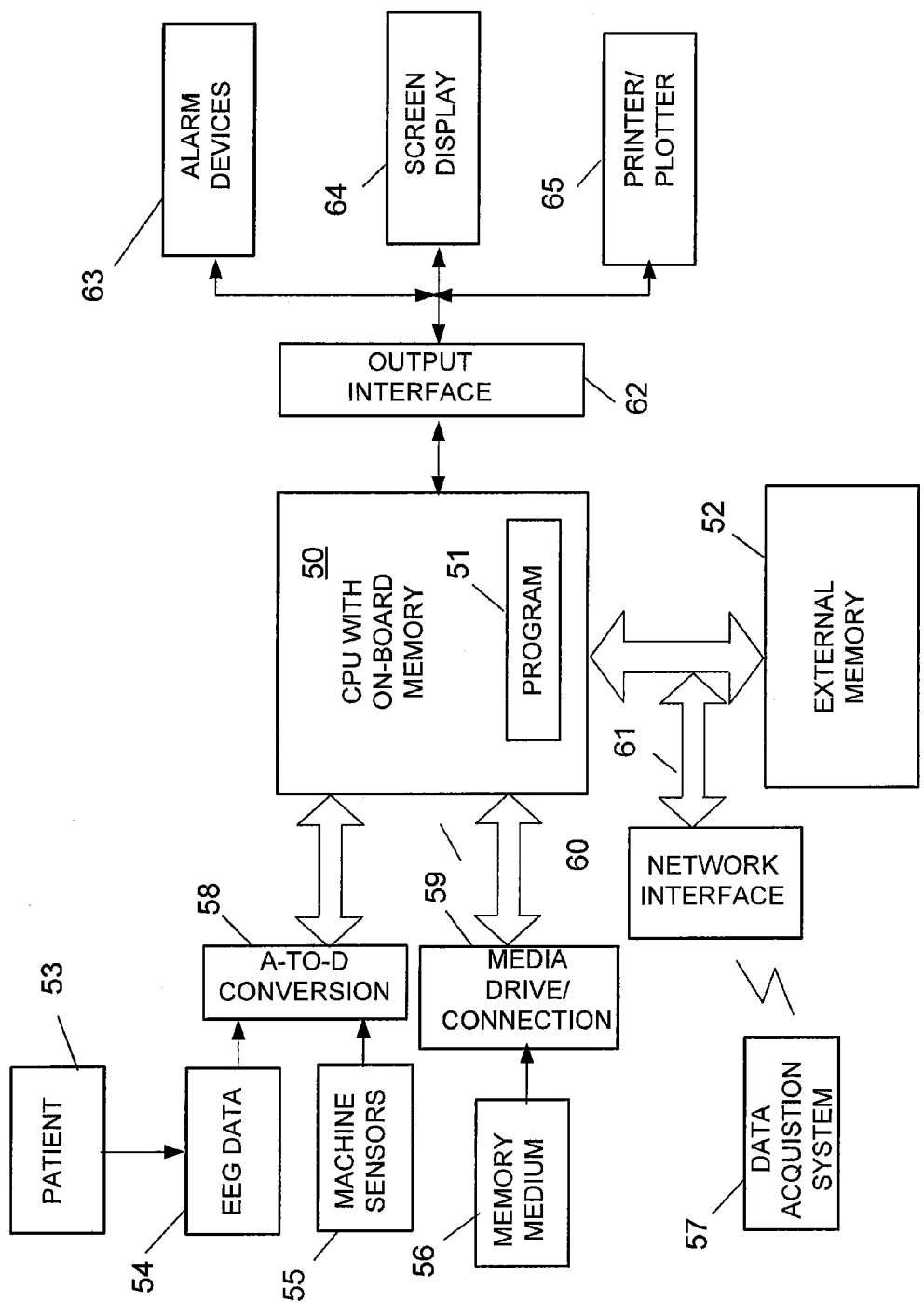
FIG. 10 is a block diagram of a computing apparatus for practicing the present invention.

The method of the invention is carried out on a computing apparatus illustrated in FIG. 10. The apparatus includes a central processing unit (CPU) 50 with on-board memory, and with external memory 52. A program of instructions 51 is stored in a non-volatile portion of the memories for execution by the CPU 50. The CPU 50 may be interfaced to sensors on a patient 53 to produce EEG data 54, for example, which is read in through suitable analog-to-digital conversion circuitry 58, so as to provide suitable data signals to the CPU 50. The CPU 50 may alternatively be interfaced through analog-to-digital conversion circuitry 58 to machine sensors 55 on a machine for receiving data on machine operation. Sensor data may also be collected offline and input on one of many types of known memory media as represented by element 56, through an interface of a media drive or media connection 59, which provides data to the CPU 50. Sensor data may also be collected offline and input from a separate data acquisition system (a separate computing apparatus) through a wireless or wired network interface 60 and through the buses 61 for conveying data to the CPU 50 and the external memory 52. The computing apparatus including the CPU 50 can be as small as a single microelectronic circuit with signal processing capabilities or the apparatus can be a handheld unit, or the apparatus can be as large as a desktop or floor standing computing apparatus. The data acquisition system can be a separate computing apparatus as well as being equipped with biomedical or machine sensors 54, 55 of the type shown in FIG. 10.

After executing the program of instructions according to the methods describe above, the CPU 50 can transmit a signal through an output interface circuit 62 of a type well known in the art to alarm devices 63, either audible or visual, to a screen display 64 or to a printer or plotter device 65. The output devices are used to provide signals of forewarnings prior to a critical event or failure event as described elsewhere herein.

This has been a description of detailed examples of the invention. These examples illustrate the technical improvements, as taught in the present invention: use of equiprobable symbols, quantitification of channel-consistent total-true rate of forewarning, various objective functions for event forewarning, different search strategies to maximize these objective functions, and forewarning of various biomedical events and failures in machines and physical processes. Typical biomedical events and data include, but are not limited to, epileptic seizures from EEG, cardiac fibrillation from EKG, and breathing difficulty from lung sounds. Typical machines include, but are not limited to, motors, pumps, turbines, and metal cutting. Typical time-serial machine data include, but are not limited to, electrical current, voltage, and power; position, velocity, and acceleration; and temperature and pressure. It will apparent to those of ordinary skill in the art that certain modifications might be made without departing from the scope of the invention, which is defined by the following claims.

I claim:

1. A method for processing data in a computing apparatus from a test subject to signal a forewarning of a critical event, comprising:
    acquiring a plurality of sets of data received from at least one channel of data for sensing a condition of at least one test subject;
    computing a composite measure of dissimilarity ($C_i$) from normalized measures of dissimilarity (U) for distribution functions derived from a connected phase space and for distribution functions derived from an unconnected phase space for each respective channel of data;
    computing a cumulative sum of the composite measure of dissimilarity ($\Sigma_i C_i$) over a series of time frames;
    applying a straight-line fit to the cumulative sum of composite measures ($\Sigma_i C_i$) using a least squares calculation;
    computing a standard deviation ($\sigma$) between the straight-line fit and the cumulative sum ($\Sigma_i C_i$);
    determining a forewarning threshold ($U_{FW}$) for detecting failure forewarnings, wherein said threshold corresponds to a minimum in said standard deviation ($\sigma$);
    determining a failure value threshold ($U_{FAIL}$) corresponding to a value of the composite measure of dissimilarity ($C_i$) that signals an impending critical event; and
    providing a visual or audible forewarning signal of the impending critical event to a human observer after either one of 1) $N_{FW}$ successive occurrences of $C_i$ above the forewarning threshold ($U_{FW}$) or 2) after $N_{FAIL}$ successive occurrences of $C_i$ above the failure value threshold ($U_{FAIL}$).

2. The method of claim 1, wherein the normalized measures of dissimilarity for distribution functions are based on data that are processed to discrete states on the basis of a slope between each pair of data points, which is either positive or negative depending on a change in the data between two points in time.

3. The method of claim 1, wherein the composite measure of dissimilarity is computed from a plurality of normalized measures of dissimilarity; and
    wherein the measures of dissimilarity include $\chi_t^2$, $\chi_e^2$, $L_t$ and $L_e$, where $\chi_t^2$ and $L_t$ incorporate a probability of changes of state in the sets of data from one time to another; and $\chi_e^2$ and $L_e$ represent a comparison of an equilibrium state to the present state in the sets of data.

4. The method of claim 1, wherein prior to the computation of the measures of dissimilarity, and in lieu of computing either a connected or unconnected phase space, a Shannon entropy is computed according to the following expression $$\Delta E = -\sum_J \{[A_J(t+\Delta t) - A_J(t)]/n\} H_J(t)$$

where E is the entropy, $A_J(t)$ is a state of the data at time t, and $H_J(t)$ is the harmonic mean.

5. The method of claim 1, wherein the test subject is at least one of a mechanical device and a physical process.

6. The method of claim 1, wherein the test subject is a medical patient.

7. A method for processing data in a computing apparatus from a test subject to signal a forewarning of a critical event, comprising:

acquiring a plurality of sets of data received from at least one channel of data for sensing a condition of at least one test subject;

computing a Shannon entropy is computed according to the following expression $$\Delta E = -\sum_J \{[A_J(t+\Delta t) - A_J(t)]/n\} H_J(t)$$

where E is the entropy, $A_J(t)$ is a state of the data at time t, and time t+$\Delta$t, and where $H_J(t)$ is the harmonic mean;

computing a composite measure of dissimilarity ($C_i$) from normalized measures of dissimilarity (U) for changes of state derived from the Shannon entropy;

computing a cumulative sum of the composite measure of dissimilarity ($\Sigma_i C_i$) over a series of time frames;

applying a straight-line fit to the cumulative sum of composite measures ($\Sigma_i C_i$) using a least squares calculation;

computing a standard deviation ($\sigma$) between the straight-line fit and the cumulative sum ($\Sigma_i C_i$);

determining a threshold for detecting failure forewarnings ($U_{FW}$), wherein said threshold corresponds to a minimum in said standard deviation ($\sigma$);

determining a failure value threshold ($U_{FAIL}$) corresponding to a value of the composite measure of dissimilarity ($C_i$) that signals an impending critical event; and providing a visual or audible forewarning signal of the impending critical event to a human observer after either one of 1) $N_{FW}$ successive occurrences of $C_i$ above the threshold ($U_{FW}$) or 2) after $N_{FAIL}$ successive occurrences of $C_i$ after the threshold ($U_{FAIL}$).

8. The method of claim 7, wherein the normalized measures of dissimilarity for distribution functions are based on data that are processed to discrete states on the basis of a slope between each pair of data points, which is either positive or negative depending on a change in the data between two points in time.

9. The method of claim 7, wherein the test subject is at least one of a mechanical device and a physical process.

10. The method of claim 7, wherein the test subject is a medical patient.

11. A method for processing data in a computing apparatus from a test subject to signal a forewarning of a critical event, comprising:

acquiring a plurality of sets of data received from at least one channel of data for sensing a condition of at least one test subject;

computing a composite measure of dissimilarity ($C_i$) from normalized measures of dissimilarity (U) for distribution functions derived from a connected phase space and for distribution functions derived from an unconnected phase space for each respective channel of data;

wherein the composite measure of dissimilarity is computed from a plurality of normalized measures of dissimilarity; and wherein the measures of dissimilarity include $\chi_t^2$, $\chi_e^2$, $L_t$ and $L_e$, where $\chi_t^2$ and $L_t$ incorporate a probability of changes of state in the sets of data from one time to another; and $\chi_e^2$ and $L_e$ represent a comparison of an equilibrium state to the present state in the sets of data; and computing a cumulative sum of the composite measure of dissimilarity ($\Sigma_i C_i$) over a series of time frames;

applying a straight-line fit to the cumulative sum of composite measures ($\Sigma_i C_i$) using a least squares calculation;

computing a standard deviation ($\sigma$) between the straight-line fit and the cumulative sum ($\Sigma_i C_i$);

determining a forewarning threshold ($U_{FW}$) for detecting failure forewarnings, wherein said threshold corresponds to a minimum in said standard deviation ($\sigma$);

determining a failure value threshold ($U_{FAIL}$) corresponding to a value of the composite measure of dissimilarity ($C_i$) that signals an impending critical event; and providing a visual or audible forewarning signal of the impending critical event to a human observer after either one of 1) $N_{FW}$ successive occurrences of $C_i$ above the forewarning threshold ($U_{FW}$) or 2) after $N_{FAIL}$ successive occurrences of $C_i$ above the failure value threshold ($U_{FAIL}$).

12. The method of claim 11, wherein the normalized measures of dissimilarity for distribution functions are based on data that are processed to discrete states on the basis of a slope between each pair of data points, which is either positive or negative depending on a change in the data between two points in time.

13. The method of claim 11, wherein the test subject is at least one of a mechanical device and a physical process.

14. The method of claim 11, wherein the test subject is a medical patient.

* * * * *